(12) United States Patent
Monzyk et al.

(10) Patent No.: US 7,527,770 B2  
(45) Date of Patent: *May 5, 2009

(54) PHOTOLYTIC OXYGENATOR WITH CARBON DIOXIDE FIXATION AND SEPARATION

(75) Inventors: Bruce F. Monzyk, Delaware, OH (US); Eric C. Burckle, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 852 days.

This patent is subject to a terminal disclaimer.

(21) Appl. No.: 10/485,934

(22) PCT Filed: Aug. 1, 2002

(86) PCT No.: PCT/US02/24277

§ 371 (c)(1), (2), (4) Date: Sep. 7, 2004

(87) PCT Pub. No.: WO03/012261

PCT Pub. Date: Feb. 13, 2003

(65) Prior Publication Data

US 2005/0013750 A1 Jan. 20, 2005

Related U.S. Application Data

(60) Provisional application No. 60/358,448, filed on Feb. 20, 2002, provisional application No. 60/388,977, filed on Jun. 14, 2002, provisional application No. 60/393,049, filed on Jun. 28, 2002.

(51) Int. Cl. *B01J 19/08* (2006.01)
(52) U.S. Cl. ................ 422/186.3; 204/252
(58) Field of Classification Search ........... 422/186, 422/186.3; 204/252
See application file for complete search history.

(56) References Cited

U.S. PATENT DOCUMENTS 3,925,212 A * 12/1975 Tchernev ............ 422/186  
4,045,315 A * 8/1977 Fletcher et al. ........ 204/157.5  
4,381,978 A 5/1983 Gratzel et al.  
6,866,755 B2 * 3/2005 Monzyk et al. ............ 204/252

FOREIGN PATENT DOCUMENTS

WO WO 01/02624 A1 * 1/2001

* cited by examiner

*Primary Examiner*—Kishor Mayekar  
(74) *Attorney, Agent, or Firm*—Richard M. Klein; Fay Sharpe LLP

(57) ABSTRACT

Apparatus for oxygenating an enclosed space as well as removing carbon dioxide from the enclosed space.

32 Claims, 9 Drawing Sheets

PHOTOLYTIC OXYGENATOR WITH CARBON DIOXIDE FIXATION AND SEPARATION

This application claims priority to and extends the teachings and disclosures of four U.S. applications: U.S. application Ser. No. 09/920,385 for Photolytic Artificial Lung, Bruce Monzyk et at, filed Aug. 1, 2001, now U.S. Pat. No. 6,866, 755; Provisional Application Ser. No. 60/358,448 for Development of Photolytic Pulmonary Gas Exchange, Bruce Monzyk, et al., filed Feb. 20, 2002; Provisional Application Ser. No. 60/388,977 for Photolyfic Artificial Lung, Bruce Monzyk et al., filed Jun. 14, 2002; and Provisional Application Ser. No. 60/393,049 for Photolytic Oxygenator with Carbon Dioxide Fixation and Separation, Bruce Monzyk, et al., filed Jun. 28, 2002. This application also claims priority to PCT Application No. PCT/US02/24277, filed Aug. 1, 2002.

FIELD OF THE INVENTION

The present invention is directed to a photolytically driven electrochemical ("PDEC") oxygenator and carbon dioxide remover that uses light energy to achieve gas exchange in various media. It finds particular application in providing a proper physiological gas environment for humans, animals and microorganisms. It is also to be appreciated that the invention finds further particular applications in confined space areas such as the crew or cabin space of a submarine, space station, interplanetary vehicle, extraterrestrial vehicle, subterranean mine, cave or tunnels or other confined volume areas.

BACKGROUND OF THE INVENTION

Oxygen depletion in confined spaces has always been a problem. Human beings need a constant supply of oxygen and the concomitant removal of carbon dioxide to live and function. When humans, microorganisms or other animals are in confined spaces where the flow of gases from the atmosphere is impeded, the aforementioned supply of oxygen and removal of carbon dioxide are critical to maintaining a proper physiological environment.

Known methods for providing oxygen generation and/or carbon dioxide removal include the electrolytic production of oxygen using KOH in water. While hydrogen and oxygen are produced, the simultaneous production of hydrogen results in problems concerning its safe capture, storage and disposal.

An organic amine liquid carbon dioxide process has also been used to capture carbon dioxide. Moreover, on an emergency basis, lithium candles have been used to produce oxygen and lithium hydroxide to absorb carbon dioxide. Other devices and processes for providing oxygen and removing carbon dioxide are briefly described below:

Chlorate Candles—These are heated to cause the decomposition of the chlorate into oxygen gas and salt. In this operation the high heat required and sudden release of large amounts of pure oxygen gas are highly hazardous and limits the usefulness of this technology.

Potassium Hydroxide (KOH) Electrolysis—This technology is also hazardous as it emits explosive mixtures of $O_2$ and $H_2$ gases, since KOH is strongly caustic and corrosive.

Lithium Hydroxide (LiOH) is used for $CO_2$ capture. However, this material is hazardous due to it being a caustic fine powder. It is spread over the floor to generate a high surface area whereupon it leads to possible contact and/or ingestion by the crew causing illness and potential lung damage.

$CO_2$ is also removed by large devices using liquid organic amines. These units are complicated processes and so are difficult to control. They also require large amounts of space and are heavy.

In addition, the first and third of the above listed technologies are "once use" technologies and so are spent after one use.

Therefore, a need exists for new technology and approaches that have the potential to provide long term life support in confined environments.

SUMMARY OF THE INVENTION

The enclosed invention uses photolytic energy to drive the production of $O_2$ gas and electrochemical fixation of $CO_2$ gas as a means to convert used, "stale" air, i.e. air low in $O_2$ and/or rich in $CO_2$ relative to atmospheric breathing into breathable air for humans, animals, and aerobic or facultative aerobic microorganisms.

More particularly, the present invention relates to a photolytically driven electrochemical (PDEC) oxygenation and carbon dioxide removal apparatus. The apparatus includes a photo-electro chemical cell ("photolytic cell" or "photolytic module") that, in part, operates similar to the photosynthesis process that takes place in green plants. In the anode compartment, the apparatus utilizes the photolytic cell to convert light energy in order to simultaneously generate oxygen and electrical energy. The photolytic cell also removes carbon dioxide from the environment and converts it to a carbonate solid in the cathode compartment. One or more photolytic cells can be included in the apparatus of the present invention depending on the quantity, quality, etc. of desired gas exchange.

The light energy utilized in the present invention is ultraviolet ("UV") light or visible light, with the laser form being the most preferred. However, the light energy can also be broad-band, received by the way of a "light pipe" fiber optic cable or by the way of an attenuated total reflectance (ATR) link.

In the apparatus, dissolved oxygen is generated in the anode compartment from an aqueous solution by means of the light dependent chemical reactions, photolysis and disproportionation. This is followed by the removal or clearing of carbon dioxide in the cathode compartment by the formation of higher carbon compositions such as hexose sugar.

In this regard, photolysis is the initiation of a chemical reaction that results from the absorbance of one or more quanta of radiation. Here, water from an aqueous solution is converted into oxygen by a light-activated catalyst, such as a semiconducting metal oxide. The metal oxide is utilized as a photo-absorbent material or a photo-absorption element. It is photolytically irradiated to form, from water, hydrogen ions, hydrogen peroxide or other forms of oxygen gas precursor (active oxygen, "AO") and electrons by the absorption of one or more quantra of electromagnetic radiation. The free electrons generated are then electrically conducted away to avoid reversal of the reaction and optionally utilized to drive various electrical devices, such as a pump.

For example, it has been found that active oxygen can be generated in one embodiment of the present invention by the use of the anatase form of titania ($TiO_{2(a)}$) as the light absorbent material in the anode compartment. The photo energy of light, such as ultraviolet laser light (about 350 nm), selectively excites $TiO_2$ semiconductor transition (about 350-390 nm band, or about 3.1 eV) with minimal material radiation or transmission. The ultraviolet energy produces charge separation in the anatase form of $TiO_2$, which then produces active oxygen (AO) and free electrons. The free electrons are then subsequently electrically conducted away due to the semiconducting property of the anatase. Alternatively, other suitable light absorbent materials can also be utilized in the present invention at various wavelengths provided that the energy is sufficient to produce active oxygen.

Moreover, the active oxygen produced during photolysis can be converted by means of manganese dioxide ($MnO_2$), or other disproportionation catalytic agents and/or processes, into dissolved oxygen (DO) and water.

Additionally, in the artificial lung of the present invention, carbon dioxide can also be removed from the environment by the means of a series of carbon molecule building reactions. These reactions occur in the cathode compartment of the apparatus to produce removable and/or recyclable carbonate solids.

Consequently, the apparatus of the present invention produces oxygen directly from an aqueous solution. At the same time, the apparatus also utilizes the hydrogen ions produced from the aqueous solution to remove the carbon dioxide to produce a carbonate solid such as hexose sugar.

A brief description of the pertinent reactions involved in the embodiment of the present invention utilizing anatase as the light absorbent material (i.e. as the photolytic catalyst and $MnO_2$ as the disproportionation catalyst) is provided below:

Photolysis:

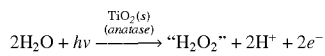

$$2H_2O + h\nu \xrightarrow[\text{(anatase)}]{TiO_2(s)} \text{``}H_2O_2\text{''} + 2H^+ + 2e^-$$

where $H_2O_2$ is used to illustrate "active oxygen" intermediate.

Disproportionation:

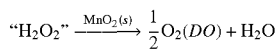

$$\text{``}H_2O_2\text{''} \xrightarrow{MnO_2(s)} \frac{1}{2}O_2(DO) + H_2O$$

DO=dissolved oxygen, which is readily converted to gaseous oxygen, $O_2(g)$, for breathable air maintenance applications.

The above information shows the general chemical reactions involved in the anode compartment of the photolytic cell to produce dissolved oxygen. Subsequent to this production, the electrons are conducted away, and the dissolved oxygen diffuses from the film surface to be collected and/or channeled to a confined environment.

Additionally, the hydrogen ions generated flow from the anode compartment to the cathode compartment. There they react with carbon dioxide and other compositions to form solid, higher carbon materials.

In a further aspect, the present invention is also directed to a photolytic cell. The photolytic cell includes a transparent substrate or window. An anode (such as a metal film) is adjacent to the transparent window. A photolytic coating containing a light-activated catalyst and a disproportionation catalyst abuts the anode. An anolyte cell flow through area is adjacent to the light activated catalyst. An optional cation exchange membrane borders the anolyte cell flow through area. A catholyte cell flow area abuts the cation exchange membrane. A cathode is present adjacent to the catholyte and is connected to the anode.

In an additional aspect, the present invention is further directed to a method for delivering oxygen to an enclosed or restricted environment. The method comprises moving an aqueous solution, such as an electrolyte solution, into a photolytic cell wherein light is utilized by a light-activated catalyst to produce oxygen from water and moving the oxygen generated out of the photolytic cell into the enclosed environment. The free hydrogen ions generated by this process can be optionally utilized to convert carbon dioxide to a carbonate solid.

In a further aspect, the present invention relates to the direct photolytic conversion of water to liquid phase oxygen (dissolved oxygen), with commensurate clearance of carbon dioxide. A test flow cell is provided comprising a conductive coating of vacuum-deposited titanium (Ti) metal, adherent $TiO_2$ (anatase), and $MnO_2$, applied as a laminant to a glass substrate. Long wavelength (low energy) UV laser light, directed to the transparent glass substrate, reproducibly resulted in the generation of $H_2O_2$, an active form of oxygen (active oxygen), which was subsequently converted, by the catalytic action of $MnO_2$, to dissolved oxygen. Oxygen gas is then extracted from the dissolved oxygen through an oxygen gas separator and collected or channeled to a closed or constricted living environment. Additionally, carbon dioxide present in the closed or constricted living environment is removed by reacting the carbon dioxide with other carbon sources and catalysts to form carbonate solids. Based on these results and others, the photolytic cell or module may be used, employing multiple parallel photolytic surfaces to improve $O_2$ yield and $CO_2$ clearance.

These and other objets and features of te invention will be apparent from the descriptions set forth below.

BRIEF DESCRIPTION OF THE DRAWINGS

The present invention will become more fully understood from the detailed description given below, the claims and the accompanying drawings. The description and drawings are given by the way of illustration only, and thus do not limit the present invention.

DETAILED DESCRIPTION OF THE INVENTION

Figure 1:
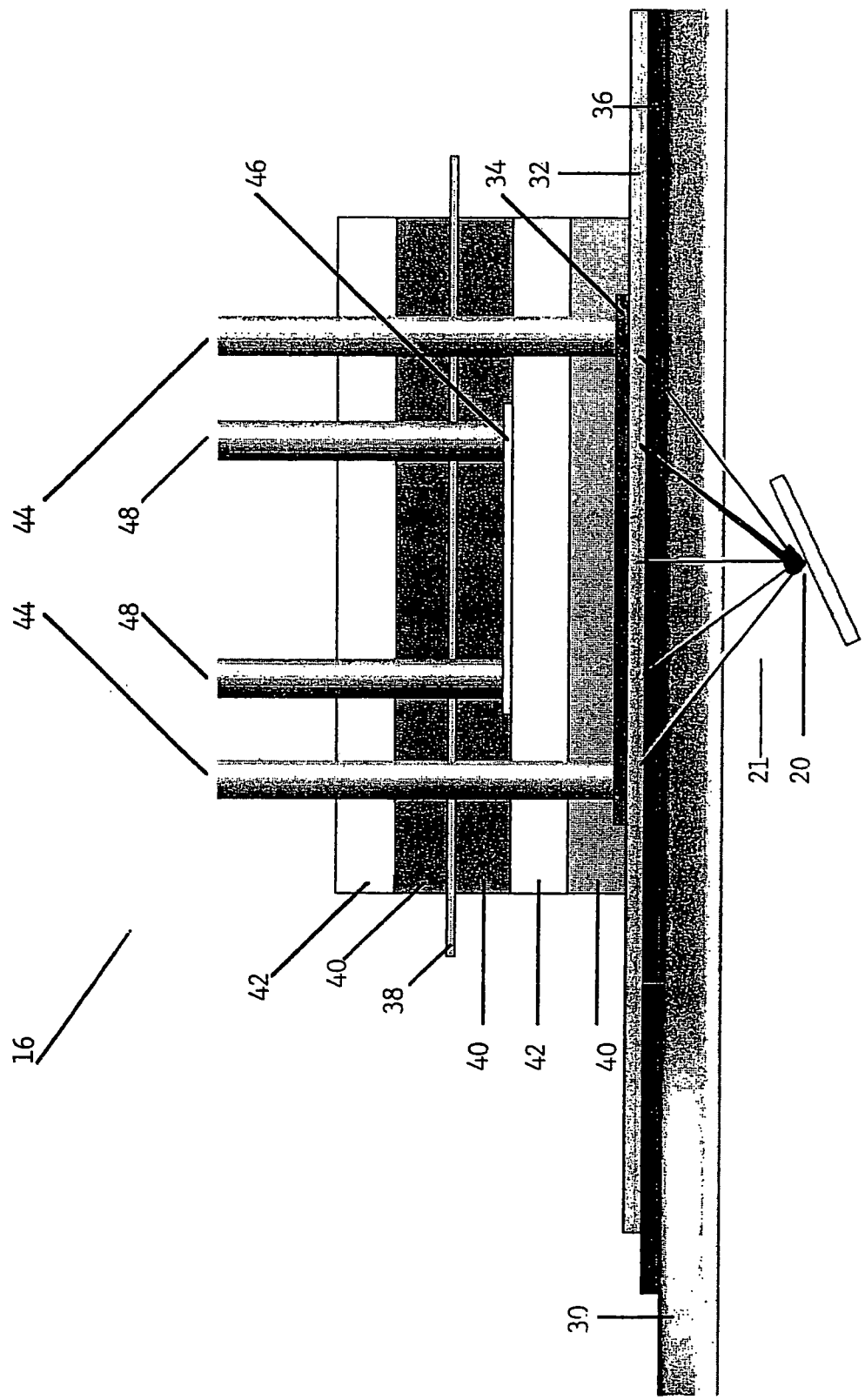
FIG. 1 shows a schematic view of an embodiment of the photolytic cell that can be utilized in the present invention.

Broadly, the present invention is directed to a photolytically driven electrochemical (PDEC) oxygenator and carbon dioxide removal apparatus. The apparatus may be used for controlling the environment in a closed or restricted volume in order to make the volume habitable to humans, animals and aerobic microorganisms. The apparatus achieves a gas balance typical for that required by the humans, animals or aerobic microorganisms in at least part of the enclosed volume.

The photolytically driven electrochemical (PDEC) oxygenator and carbon dioxide removal apparatus includes a photo-electrochemical cell (or photolytic cell) that in part operates similar to the photosynthesis process that takes place in green plants. The photolytic oxygenator apparatus utilizes the photolytic energy to drive oxygen generation from water. The oxygen is then released to the confined volume. The photolytic cell also converts carbon dioxide to a $C_6$ sugar-type compound that can be stored as a solid, gel or liquid, which then fixes the $CO_2$ thereby removing it from the confined space. This sugar-type compound can optionally be recycled in the form of a food or energy source.

In this regard, oxygen is produced in the anode side of the PDEC apparatus of the present invention. The oxygen produced at the anode side of the photolytic oxygenator apparatus is typically produced in an aqueous electrolyte solution such as a brine, seawater, etc. The oxygenated liquid so formed then flows out of the photolytic oxygenator apparatus. It is degassed and the oxygen gas is sent back to the closed or restricted volume area for breathing by humans, animals or aerobic microorganisms.

The carbon dioxide is removed by the cathode side of the PDEC apparatus of the present invention. Gas containing carbon dioxide from the enclosed volume is reacted with an aqueous liquid at pH>4, and preferably >6, to extract carbon dioxide into the liquid so that it can be fixed by formation of glycerate, which is transported and treated in the cathode portion (or cathode compartment) of the photolytic cell to form a solid, sugar-like compound.

In an additional embodiment, the present invention is directed to the use of a photolytic cell as a novel respiratory assist device and process. The apparatus of the invention includes one or more photolytic cells having photochemically active material and associated components for the production of oxygen, the removal of carbon dioxide, and the co-production of electrical power. The electrical power can be used to produce additional chemical changes or reactions. Optionally, the invention may include a photolytic chamber to house or hold a sufficient number of stacked or assembled photolytic cells to perform the rate of gas exchange desired.

In one embodiment of the present invention, a semi-conducting metal. oxide is used as the photo-absorption element. This semi-conducting metal oxide is the anatase form of titania, or $TiO_2$. Photolysis of this oxide results in the generation of active oxygen, in a manner, which is considerably more long lasting than photosynthetic pigments (i.e. the chlorophiles). Importantly, the light energy associated with activation by a 354 nm UV laser light selectively excites the $TiO_2$ semiconductor electronic transition (350-389 nm band, or about 3.2 eV) with minimal wasted radiation or transmission. Special dopants may adjust this wavelength, in order to reduce the energy requirement and even to allow activation within the range of visible light. UV energy produces charge separation in the anatase, which then produces active oxygen, hydrogen ions and free electrons, the latter being electrically conducted away. Diffusion layers are minimized through the use of electron conductance to and from the photolytic site by photolytic transparency and by electrochemical conduction.

The active oxygen is then converted to dissolve oxygen through the use of a disproportionation catalyst such as $MnO_2$. Importantly, this apparatus has the ability to efficiently generate both fluid phase oxygen (i.e. dissolved oxygen) and gas phase oxygen (i.e. $PO_2$).

Taken from a broad perspective, the present invention includes the following system components: 1) a sensitive and complex aqueous phase, 2) photolytic energy to provide "charge separation" in a thin film, 3) electrical energy, produced from the electrons of the "charge separation" photolytic reaction, 4) chemical reactions driven by the photochemistry, i.e. DO generation, and 5) the removal of $CO_2$ through the generation of carbonate solids.

The invention can also use mesoporous, amorphous, microporous, crystalline, heterogeneous, or homogenous materials and coatings, and the like, alone or in combination to provide high-surface area active coatings to photolytically drive chemical changes, photochemical changes, electricity generation, and/or electrochemical changes in fluid streams, preferably adjacent to the coating/material, or, in the case of electricity, electrical current driven into wires attached to the coating directly, or via a electrical conducting intermediate material. The said fluid can be liquid or gas or sol gel or conducting solid or porous solid.

FIG. 1 shows one of the flow-through embodiments of the photolytic cell 16 of the present invention. In this flow-through cell embodiment, the following main components of the photolytic cell 16 are assembled, i.e. a conductive coating of vacuum deposited Ti metal 36, a coating of adherent $TiO_2$ (anatase) 32, an optional $MnO_2$ particulate layer 34. A UV laser light 20 was shown on the transparent glass or quartz substrate 30 so to initiate the reactions.

In this regard, the photolytic cell 16 of FIG. 1 includes a transparent window 30 or wave guide for the entry of light energy in the form of photons 21 from a light source 20 such as an ultraviolet laser light. On one side of the glass slide is an anode conductor layer 36, such as titanium (Ti) metal film. Attached to the anode conductor layer 36, is a layer of a light activated catalyst 32 such as anatase ($TiO_2$). An optional catalyst layer 34, such as manganese dioxide, is adjacent to the light activated catalyst layer 32. The photolytic cell 16 includes one or more layers of silicone gaskets or spacers 40 and an acrylic housing 42. A pair of anolytes 44 (in/out) are connected to the light activated catalyst layer 32 or optional catalyst layer 34 and extend through the photolytic cell 16 away from the transparent window 30. The photolytic cell 16 further includes a cation exchange member 46, such as a NAFION® membrane from DuPont. A pair of catholytes 48 (in/out) are connected to the cation exchange member 46 and extend outwardly through the photolytic cell 16 generally away from the transparent window 30. The photolytic cell 16 further includes a cathode layer 38, such as Pt foil, adjacent to the cation exchange member 46. The operation and use of this embodiment of the invention is more particularly described below.

Figure 2:
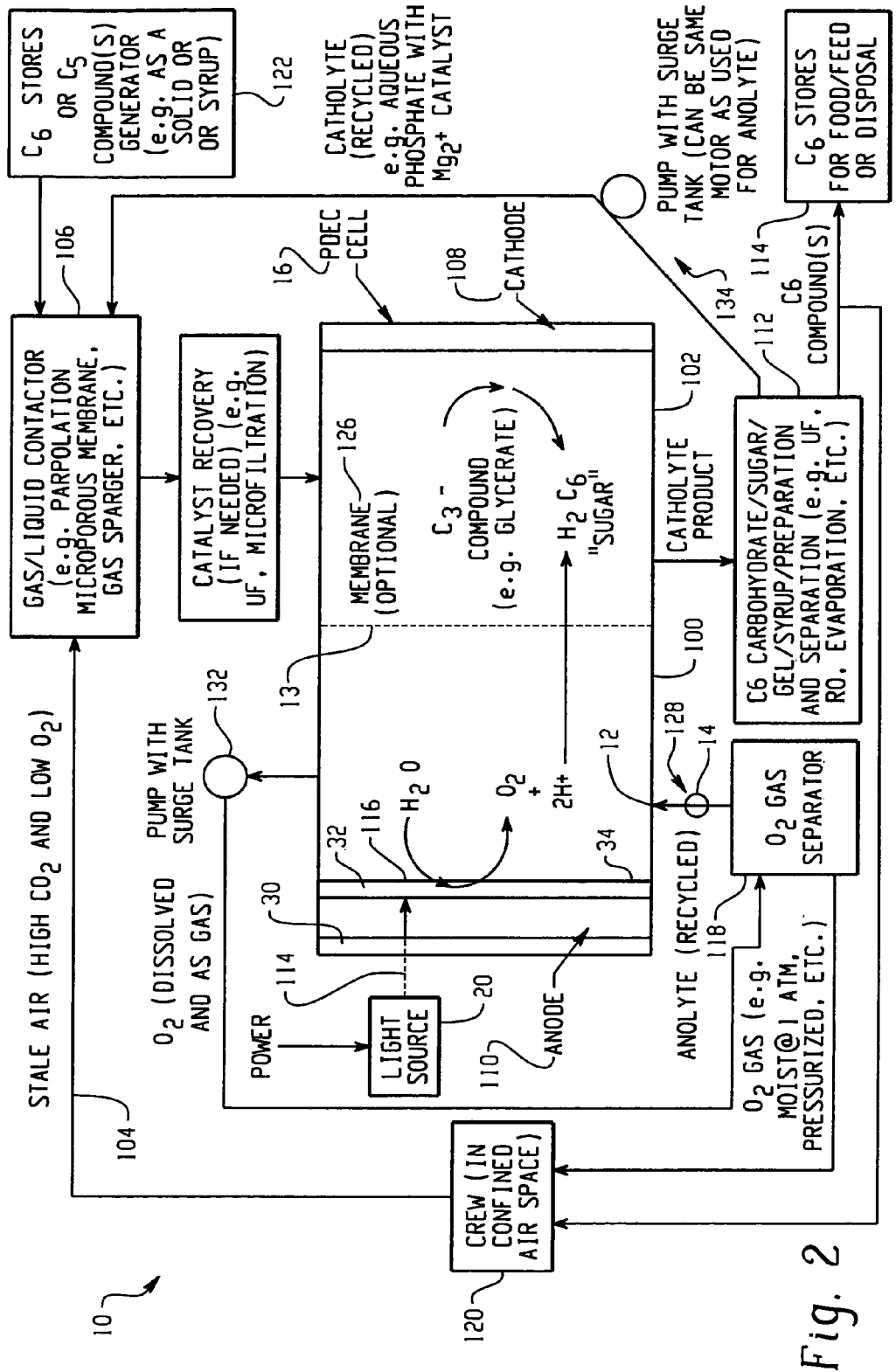
FIG. 2 is a schematic of a generalized embodiment of the invention wherein an alpha-keto pentose source is used to remove carbon dioxide.

FIG. 2 is a schematic drawing showing the electrical and chemical transformations which occur in the PDEC cell 16 of the apparatus 10. Electrolyte or anolytye 128, such as NaCl brine, $NaSO_4$, $K_2SO_4$, HCl, and the like enters the anode compartment 100/44 of the photolytic cell 16 through inlet 12 by way of an optional peristaltic pump 14. Light photons (hv) 21/114 generated by light source 20 enter through a transparent window 30 or waveguide and activate the light activated catalyst 32 present in photo-reactive surface 116 such as 100 µm $TiO_2$ (anatase). The light activated catalyst 32 either directly converts water in the electrolyte 128 to dissolved oxygen or converts water to active oxygen and hydrogen ions and an optional second catalyst 34, such as manganese dioxide ($MnO_2$) on a porous film, converts active oxygen (e.g. $H_2O_2$) into dissolved oxygen (DO). The oxygen then exits the anode compartment 100/44 by the way of outlet 13 and is pumped by an optional pump 132 to oxygen gas separator 118. At the gas separator 118, the gaseous oxygen is provided to a confined air space 120 for usage.

The electrons released from the conversion of water from the electrolyte to oxygen are collected in the collector electron anode 110. An electrical current formed from a battery or other source (not shown) allows the electrons to flow from the anode 110 to the cathode 108, such as graphite or nickel, so that the electrons do not react with the active oxygen to cause a back reaction and the reformation of water.

The electrical current and electron flow can be regulated by a current regulator or resistor (not shown). The hydrogen ions formed from the conversion of water at the light activated catalyst diffuse from the anode compartment 100/44 across the optional membrane 126 to the cathode compartment 102/48.

In the cathode compartment 102/48, stale air 104, which is rich in $CO_2$ relative to atmospheric breathing air, is contacted with i) a liquid such as brine containing α-keto pentose containing a catalyst typically of mixtures of $Mg^{2+}/PO_4^{3-}$ electrolyte to convert carbon dioxide into dissolved form in the liquid; and ii) $C_3$ pentose obtained from stores 122 which also contains a catalyst to form glycerate or the equivalent. The glycerate is electrochemically reduced at the surface of the cathode and reacts with the hydrogen ions which previously immigrated from the anode compartment 100 to the cathode compartment 102 to form a hexose ($C_6$) sugar. The hexose sugar solution then flows out of the cathode compartment 102 into separator 112. In separator 112, the liquid is separated and then recycled 134 and the hexose sugar is placed in $C_6$ stores 114 or utilized as an energy source for the crew, etc.

The various particular components and/or processes of the flow through PDEC cell embodiment of the present invention are described in more detail below:

1. Transparent Substrate or Window 30

The transparent window 30 can be formed from glass, quartz slides, quartz, etc. Glass is useful in forming the transparent window provided that the UV transparency is adequate at the wavelength needed. Quartz slides are also useful because of its high UV transparency. For the transparent window, light entry into and through the transparent window can be from the back, side, or bottom. Edge illumination through the transparent window can optionally include a lens or wave guide.

The transparent window can further include a wave guide. A wave guide uniformly distributes photons (hv) from the light over the surface of the light activated catalyst. Particularly, the wave guide causes the light photons to travel in a path so that the photons maximally contact the entire layer of the light activated catalyst. Light enters the wave guide in the side of the transparent window generally parallel to the surface of the light activated catalyst that is attached to the transparent window. The wave guide allows for maximal light photon contact with the light activated catalyst without directly illuminating the side of the entire light activated catalyst attached to the transparent window. The wave guide also allows form maximal photolytic cell staking because light is not required to directly illuminate the light activated catalyst but rather can be indirectly illuminated by side or edge entry in the transparent window. The wave guide provides additional efficiency to light used in the photolytic cell because the light can be spread across the entire surface of the light activated catalyst.

2. Anode Conductor Layer 110

The anode conductor layer 110 conducts electrons formed from the reaction of water to oxygen out of the anode. The anode conductor layer prevents the electrons from reacting back with the oxygen to reform water, thereby allowing maximal formation of oxygen. The anode conductor layer is applied or attached to at least one side of the transparent window 30.

The anode conductor layer 110 can be formed at least two different ways. The anode layer can be formed by attaching a thin film of uniform metallic conductor to the transparent window using vapor deposition. The film preferably has a thickness of less than about 0.2 µm. Preferably, the film is formed from gold or titanium. Gold remains metallic at all conditions but can be very efficient at UV light blockage or reflection. Titanium can be oxidized to $TiO_2$ by adding $O_2$ to the deposition chamber to yield a possible catalyst layer with excellent adhesion.

The anode conductor layer 110 can also be formed by using photo-resist technology. Under photo-resist technology, grids are prepared with masks using vapor deposition. Conductor line spacing, width and thickness optimization may be required to prevent excessive attenuation, and provide sufficiently close conductive areas to sweep electrons away from the light activated catalyst layer.

3. Catalysts 32 and 34

A light activated catalyst 32 is coated onto the anode conductor layer. The light activated catalyst is photochemically activated and reacts with water to form dissolved oxygen or a free radical oxygen intermediate that is ultimately converted to dissolved oxygen. The term active oxygen (AO) in the present application defines any free radical oxygen intermediate formed in the photolytically catalyzed reaction of water that is ultimately converted to dissolved oxygen. The active oxygen formed is in the form of a peroxide, such as hydrogen peroxide, $H_2O_2$, or peroxide ion salt, hydroxyl free radical, super oxide ion, etc., and is converted into dissolved oxygen in the presence of a catalyst. The active oxygen formed depends on the light activated catalyst used. Also, depending on the light activated catalyst used, water may be photolytically converted directly into dissolved oxygen without first forming an active oxygen.

Several different catalysts can be employed for producing dissolved oxygen photochemically. One catalyst that can be used to photochemically produce oxygen is zinc oxide. By using zinc oxide, peroxide ($H_2O_2$) is produced directly from water. $H_2O_2$ is an excellent form of active oxygen for providing sufficient potential diffusion distance, and also for the disproportionate reaction to dissolved oxygen and water via a solid $MnO_2$ catalyst (similar to green plant $O_2$ generation site) occurring photochemically at <340 nm by way of metal ion assisted disproportionation with catalase and other hydroperoxidases. Zinc oxide film has other positive attributes including, known film formation technology (e.g. via the zinc/nitrate/glycine reaction), low toxicity concerns, and low cost.

An additional catalyst that can be used to photochemically produce dissolved oxygen is tungstate ($WO_3$) that is exposed to visible light and using $e^-_{scb}$ removal. $WO_3$ yields oxygen ($O_2$) directly from water without the need to first produce an active oxygen species. Oxygen is generated stoichiometrically and the "back reaction" is unfavored so that there is not significant competition to the direct formation of dissolved oxygen. Only visible light is needed to generate dissolved oxygen from $WO_3$, no more than about 496 nm. $WO_3$ films present low toxicity concerns. Preferably, the use of $WO_3$ further includes the removal of excess $e^-_{scb}$ formed during oxygen formation from water.

Another catalyst suitable for reacting with water is $TiO_2$ (anatase) irradiation with, followed by dissolved oxygen production at a metal catalyst, such as a $MnO_2$ catalyst, or other similar catalyst. $TiO_2$ removes the $e^-_{scb}$ efficiently from the production area in order to ultimately obtain good dissolved oxygen production and minimize any back reaction to reform reactants. The removal of $e^-_{scb}$ is performed through conduction via the semi-conductor property of the $TiO_{2(a)}$ with enhancement via application of a small DC bias voltage. $TiO_2$ irradiation also presents low toxicity concerns. $TiO_2$ provides very high insolubility and kinetic inertness to minimize dissolution and fouling during use and maintenance. Preferably, UV light is chopped or pulsed during $TiO_2$ irradiation to allow time for the chemical reactions to occur since with continuous irradiation causes the $e^-_{scb}$ to accumulate and force a back reaction to form water. A pause in the irradiation allows time for the slower, but still extremely fast irradiation in the range of @sec to msec to occur is to occur.

A further catalyst for reacting with water to ultimately form dissolved oxygen is a semiconductor powder (SCP)-filled UV/VIS light transparent thermoplastic film. SCP-filled thermoplastic film is relatively inexpensive to manufacture and form into shape. SCP film is easily moldable, extrudable, cut and machined. SCP can be used very efficiently in surface applied only form. Also, SCP has low toxicity concerns. Optimized commercial products (conductive plastic filler powders) are available with good properties for dispersion, particle-to-particle electrical conductivity (for $e^-_{scb}$ removal), and resistance to sloughing off that can be used with the present apparatus.

The following additional preferred conditions may be used for each of the above-mentioned catalysts. First, an application of a small (e.g. up to a few volts DC) bias voltage can be applied to help ensure that the $e^-_{scb}$ is quickly conducted away from the production site. Second, a chopped illumination, instead of a continuously applied illumination, may allow secondary chemical reactions to occur since the secondary chemical reactions are slower than the photochemical reactions and enhance photo yields by allowing the excited electrons to exit the system and not be present for regeneration of starting material, i.e., water.

Of the above-mentioned catalysts, the $TiO_2$ (anatase) catalyst followed by a second metal catalyst for disproportionation is the most preferred. When the $TiO_2$ catalyst is used, the light-titania interaction is the first step in the ultimate formation of dissolved oxygen. It is known that surface hydrated particulate $TiO_2$ (anatase) solid, $TiO_{2(a)}$—$OH_2$ or $Ti^{IV}O_{2(a)}$—OH, is an efficient UV light (hv) acceptor at wave lengths <390 nm, resulting in active oxygen formation from sorbed water and hydroxyl groups. The most probable reaction is believed to be:

$Ti^{IV}O_{2(a)}$—OH+hv→$Ti^{III}$—°OH*

It is noted that other bonds to Ti have been omitted for clarity. The reactant and product of the above reaction are solid materials. In the above reaction, $H_2O$ is already bonded to the surface of the $TiO_{2(a)}$ catalyst as $H_2O$ or as hydroxyl ion ($OH^-$), i.e. $Ti^{IV}O_{2(a)}$—$OH_2$ or $Ti^{IV}O_{2(a)}$—OH, respectfully. Hence, no atoms are required to move during the very fast photon absorption process. The * represents a low lying excited electronic state where the energy of the photon is used to transition or excite an electron from a nonbonding orbital on the oxygen to a molecular orbital centered on the titanium ion, hence converting the titanium into a trivalent oxidation state. The molecular orbital centered on the titanium ion is known to be a part of the semiconduction band ("scb"), and so the electron is readily conducted away from the site to form a bipolar charged grain, or, if connected to a closed DC electrical circuit, resulting in full charge separation, i.e., $Ti^{III}$—°OH*→$[Ti^{IV}$—°OH$]^+$+$e^-_{(scb)}$↑

If the $e^-_{scb}$ is not conducted away or otherwise removed by reaction with an oxidant present in the solution, the $e^-_{scb}$ could react with the hydroxyl free radical and reverse or back react so that the system would return to its original state and form water. In this latter case there would be no net reaction and the photolytic energy will appear as a small amount of heat. Hence the charge separation process and removal of $e^-_{scb}$ is considered an important first step of the photolytic cell dissolved oxygen generation process.

The hydroxyl free radical (°OH) group present is used to represent the initial form of the active oxygen generated by the photolytic process. It is not certain that °OH is the dominant species present when $TiO_{2(a)}$ is photolyzed. The active oxygen formed could generally be in the form of a superoxide, hydrogen peroxide, or a hydroxyl free radical. However, the form of this active oxygen produced has sufficient thermodynamic driving force to form active oxygen from water. For the $TiO_{2(a)}$ catalyst at neutral pH, these highly reactive hydroxyl free radicals either back react as described above, or rapidly dimerize to form (µ-peroxo) titanium (IV) and hydrogen ions, i.e.

$$2Ti^{IV}-{}^*OH \xrightarrow{Fast} Ti^{IV}-O-O-Ti^{IV} + 2H^+$$

Another way to increase the amount of dissolved oxygen production in the $TiO_{2(a)}$ system is to provide a means to speed the rate of release of the trapped µ-peroxide as hydrogen peroxide as to active oxygen.

$Ti^{IV}$—O—O—$Ti^{IV}$+$H_2O$→$Ti^{IV}$—O—$Ti^{IV}$+$H_2O_{2(aq)}$ $H_2O_2$ is an excellent form for the active oxygen species as it readily migrates and is easily catalyzed to disproportionate into dissolved oxygen and water.

$$2H_2O_{2(aq)} \xrightarrow[fast]{Catalyst} O_{2(aq)} + 2H_2O$$

Therefore, for the $TiO_{2(a)}$ photocatalyst to be useful, a means for releasing the µ-peroxide energy is needed, such as soluble $H_2O_2$, since $H_2O_2$ can diffuse to the $MnO_2$ for dissolved oxygen production, or by conducting the oxidizing power to another active oxygen form, such as SFRs in the adjacent solution that can be used in dissolved oxygen production, or using the $Ti^{IV}$—O—O—$Ti^{IV}$ content to electronically remove electrons from the $MnO_2$ cluster/particle (as is done in green plant photosynthesis by the "D" protein). In the last means, only an electron flows from the water through the $MnO_2$ to the µ-peroxo linkage through delocalized bonds. This electron replaces the $e^-$ lost from the $TiO_{2(a)}$—OH system as $e^-_{scb}$.

The formation of $H_2O_2$ as the active oxygen is valuable since $H_2O_2$ can be rapidly converted to dissolved oxygen in 100% yield using many different methods: thermally; metal ion catalysis; particulate/surface catalysis; base catalysis; and free radical reaction with reductant initiation. Preferably, metal ion catalysis, such as, $MnO_{2(S)}$, provides an efficient catalyst for $H_2O_2$ disproportionation to water and $O_2$, on thin film substrate constructs.

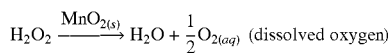

$$H_2O_2 \xrightarrow{MnO_{2(s)}} H_2O + \frac{1}{2}O_{2(aq)} \text{ (dissolved oxygen)}$$

Photo catalyst systems such as zinc oxide, ZnO, release peroxide as the active oxygen more readily than does $TiO_2$. Less acidic metal ions under the Lewis acid/base theory definition cannot sufficiently stabilize the highly alkaline peroxide ion relative to water protonation ($pK_{a1}$ of $H_2O_2$ is 11.38 (25° C.)) to form it within the solid phase, and so hydrogen peroxide, $H_2O_2$, is readily formed from ZnO:

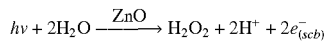

$$h\nu + 2H_2O \xrightarrow{ZnO} H_2O_2 + 2H^+ + 2e^-_{(scb)}$$

ZnO films and particles can be prepared in a number of ways with varying but controlled composition, morphology and porosity. For example, mirrors of zinc, doped zinc, and zinc alloys and can be sputtered down onto an optically transparent support, followed by oxidation with $O_{2(g)}$. This treatment produces a metal/metal oxide (Zn/ZnO) film. Another highly effective approach to semiconducting ZnO-based films is to utilize a process for optical glass coatings. (L. R. Pederson, L. A. Chick, and G. J. Exarhos, U.S. Pat. No. 4,880,772 (1989).) The optical glass coating technique is based on applying a zinc nitrate/glycine aqueous solution as a dip or spray, followed by drying (110° C. for 15 min), then heating (450-500° C. for 3 min) to initiate a self-oxidation reaction during which the carbon and nitrogen exits as gases leaving an adherent yet porous film bonded to the underlying surface (e.g. glass) and is referred to as the glycine nitrate process. (L. R. Pederson, L. A. Chick, and G. J. Exarhos, U.S. Pat. No. 4,880,772 (1989).) The ZnO film is normally produced doped with alumina by including aluminum nitrate in the aqueous formulation for the initial dip. Many other metal ion blends are also possible with this technique.

Tungstate only requires visible light to produce dissolved oxygen, and produces dissolved oxygen directly without requiring a second catalyst to form dissolved oxygen. The lower photon energy requirement for $WO_3$ is due to the smaller band gap of 2.5 eV versus at least 3 eV for $TiO_{2(a)}$. As with the $TiO_2$ anatase system, high yields are possible with the $WO_3$ catalyst if the $e^-_{scb}$ is removed. The production of $O_2$ increases very significantly if $RuO_2$ (ruthenium oxide) is placed on the surface of the $WO_3$. This is consistent with the fact that $RuO_2$ is a known good catalyst for $O_2$ production and so represents a route to improving other approaches.

An advantage may exist if the dissolved oxygen producing film could be a filled plastic. Such materials are often inexpensive and manufactured easily. Commercial sources exist for semi-conducting, low light absorbing, inorganic fillers for plastics which are supplied in ready made condition for incorporation into plastics, making the plastics electrically conductive. For example, E.I. duPont Nemours, Inc. sells electroconductive powders (EPC) under the trade name ZELEC® ECP for such purposes. The conductive substance in ZELEC® ECP is antimony-doped tin oxide ($SnO_2$:Sb). The bulk of these materials, onto which the conductor is coated, are familiar inorganics such as mica flakes, $TiO_2$, and hollow silica shells, or ECP-M, ECP-T and ECP-S respectively. Pure $SnO_2$:Sb-based material is designated ECP-XC and is a much smaller particle than the other materials. About 25-45% by weight of the ECP products are used so that the particles are sufficiently close to each other to provide internal electrical connections throughout the otherwise non-conducting plastic. ECP-S and ECP-M normally perform best for lower concentrations. Thin films of ECP-XC can provide an attractive coating because they are very fine grained and strongly light absorbing.

The $TiO_2$ layer can be formed a variety of ways. The $TiO_2$ layer can be formed by sol gel, drying and baking. A product under the trademark LIQUICOAT® from Merck & Co., Inc., which hydrolyzes $Ti(OR)_4$ type material in water to form $TiO_2$ and 4ROH can be used to form the $TiO_2$ layer under a sol gel/drying/baking process. $TiO_2$ can also be formed from preparing an anatase suspension from dry powder, then dipping, drying, and baking the suspension to form the $TiO_2$ layer. Another way the $TiO_2$ layer can be formed is by e-beam evaporating titanium and subsequently exposing the titanium to $O_2$ within a deposition chamber. The $TiO_2$ layer can also be formed by adding titanium salt to water and adjusting the pH to ~2-7 to form a suspension, then dipping the suspension and allowing the suspension to dry.

Active oxygen is created from $TiO_2$ by irradiation with UV light, but the chemical form of the active oxygen is very reactive and can be lost by side reaction occurring in close proximity to the $TiO_2$ particle surface where active oxygen is generated. There are at least three ways to minimize the loss of active oxygen to unwanted side reaction: 1) move the active oxygen to dissolved oxygen conversion point closer to the active oxygen generation point, i.e. move the metal ion catalyst as close as possible to the $TiO_2$, which may require intimate contact between these two materials, in the order of angstroms; 2) electrically connect the two points, as is done in photosynthesis by a protein capable of conducting electrons; or 3) convert the active oxygen into a longer lived intermediate active oxygen species that has time to migrate to more distant $MnO_2$ centers for conversion to dissolved oxygen.

The amount of active oxygen lost by side reactions can be minimized by introducing an active oxygen carrier molecule into the media, or "D," by analogy to a photosynthetic system. Agents for use with species D can be selected from two groups, those that readily form organic peroxides, and those that form "stable" (i.e. long-lived) free radicals. Organic peroxides are useful because they easily produce dissolved oxygen when contacting $MnO_2$, and readily form by oxygen insertion. The organic peroxide reactions are as follows:

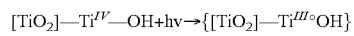

$$[TiO_2]—Ti^{IV}—OH + h\nu \rightarrow \{[TiO_2]—Ti^{III}°OH\}$$

where the excited electronic state corresponds to the ligand-to-metal charge transfer (free radical pair), and is followed by the reaction:

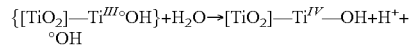

$$\{[TiO_2]—Ti^{III}°OH\} + H_2O \rightarrow [TiO_2]—Ti^{IV}—OH + H^+ + °OH$$

where conduction of the e− into the semiconductor conduction band and away from the side of the particle near the °OH prevents recombination of that e−. As shown in the reaction above, the $TiO_2$ anatase is regenerated. The above reaction produces a hydrogen ion for eventual $CO_2$ removal. Also, the active oxygen produced in the above reaction is in close proximity to $TiO_2$ as a free radical hydroxyl groups, °OH.

As °OH is extremely reactive, lasts only for a very short time and does not diffuse far. One way to increase the amount of time that °OH is present is by introducing a species that stabilizes the °OH. Similar to photosynthesis, a species "D" is introduced into the test system to capture the hydroxyl free radical in a longer lived species. The species D is generally shown the in following chemical reaction:

where D can be RC(O)OH:

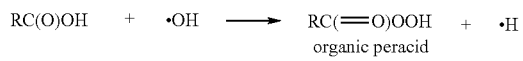

or D can be R₃COH:

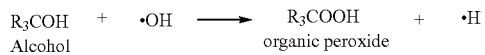

or D can be a free radical scavenger that forms a stable free radical:

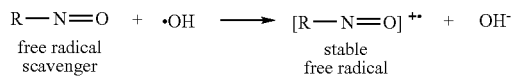

or D can be 2,6-di-tertbutyl phenol:

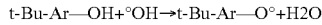

The 2,6-di-tertbutyl phenol is the most desired D species, as a strongly reducing °H radical is not formed that would consume OH⁻ and [TiO₂]—Ti$^{III}$ in wasteful reactions, regenerate the starting materials, and result in a low photochemical yield.

The catalyst used to convert active oxygen into dissolved oxygen includes metal ions capable of redox cycling, such as Fe$^{II}$, Fe$^{III}$, Cu$^{I}$, Cu$^{II}$, Co$^{II}$, Co$^{III}$, Mn$^{II}$, Mn$^{III}$, Mn$^{IV}$, etc., or metal oxides formed from metal ions capable of redox cycling, such as manganese dioxide, MnO₂. The present reaction produces dissolved oxygen directly from water and by-passes the gaseous state. The MnO₂ catalyst is most preferred because it forms dissolved oxygen efficiently and is not highly selective of the active oxygen form.

One way to facilitate the conversion of active oxygen to O₂ is by doping the surface of the TiO₂ anatase with manganese (Mn). Surface doping the TiO₂ with Mn provides a highly productive active oxygen to O₂ conversion catalyst. Active oxygen disproportionation is rapid when dropped on a Mn-doped anatase. Alternatively, active oxygen can also be converted to O₂ by placing MnO₂ on the surface of the anatase in conductive form. In this form, electrons are catalytically passed from water to the active oxygen region of the anatase. Such an arrangement more closely mimics photosynthesis O₂ production.

Another way to convert active oxygen to O₂ in the photolytic cell is by using a MnO₂ octahedral molecular sieve (MOMS) material as the dissolved oxygen catalyst. The MOMS material has an open gel-like structure and is closely related to zeolites in structure. The MOMS material is easily formed from manganese salts through precipitation and drying.

Active oxygen may also be converted to O₂ in the photolytic cell by a superoxide dismutase (SOD) catalyst. SOD catalyst is already available in the human body and can provide the required conversion of active oxygen, e.g. as O₂⁻, into a dissolved oxygen precursor, i.e. H₂O₂, to supplement the photolytic cell and Mn-doped anatase.

Alternatively, quinone can be replaced with Fe(CN)₆³⁻. The quinone or Fe(CN)₆³⁻ Q could be in homogeneous solution or film form.

4. Membrane 126

The cation exchange membrane 126 allows for the diffusion of cations in the photolytic cell. Particularly, the cation exchange membrane allows a cation, such as a hydrogen ion (H⁺) from water to diffuse through the membrane and subsequently react in the catholyte. The cation exchange membrane is commercially available under the trademark NAFION® and is available from E.I. du Pont Nemoirs Inc. NAFION® cation exchange membranes are a perfluorosulfonic acid/PTFE copolymer in an acidic form. Although NAFION® cation exchange membranes are the preferred membrane, one skilled in the art would recognize that other cation exchange membranes are also suitable in the photolytic cell.

The anodic compartment of the photolytic cell has the following series of reactions:

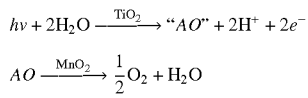

The two electrons formed in the anodic reaction are conducted away to the cathode via the anode conductor layer. The two H⁺ ions are moved to a catholyte via a cation exchange membrane.

In a further embodiment of the invention, where optionally used, the cation exchange membrane allows for the diffusion of cations in the photolytic oxygenator apparatus. Particularly, the cation exchange membrane allows a cation such as Na⁺, K⁺, H⁺, Mg²⁺, Li⁺, NH₄⁺, NR₄⁺, CR=CH₃— produced during the oxygen making step to diffuse through the membrane and subsequently form a C₆ compound from either two C₃ compounds or from a C₅ compound and CO₂.

5. Catholyte 108

The two hydrogen ions react with the electrochemically reduced glycerate in the cathode compartment 102 to produce hexose sugar (C₆) and like compositions.

6. Light Supply 20

The light supply is used in the photolytic cell to provide the photon energy necessary to activate the catalyst converting water into oxygen. The light source can be from any known light source including, but not limited to, sunlight, UV light, laser light, incandescent light, etc., depending on the activation requirement for the light activated catalyst used.

The light source may provide a particular wavelength of light depending upon the catalyst used. When tungstate (WO₃) is used as a light activated catalyst, the light source exposes visible light in order to activate WO₃. When TiO₂ or ZnO is used as a light activated catalyst, the light source used has a wavelength in the UV range.

Preferably, the light source used in the cell is a laser light. The wavelength of laser light can be manipulated in order to attain a higher efficiency in exciting the light activated catalyst and forming active oxygen. Also, laser light allows the photolytic artificial lung to dissipate less overall heat. The laser light can be directed in a small area to energize the light activated catalyst and avoid contact or irradiation with other components of the cell. A particularly preferred laser light that can be used to activate $TiO_2$ is an argon laser at 364 nm (400 mwatts/cm$^2$), which has a total power of about 2 watts, although other UV sources, including an HG arc lamp at 365 nm line, are also available.

It is preferred that the light from the light source be evenly spread within the photolytic cell. The even spreading of the light from the light source allows for maximal excitation of the catalyst in order to convert more water into either active oxygen or dissolved oxygen. Along these lines, light from the light source can enter the photolytic cell through the transparent window from many positions. Light from the light source can enter directly through the transparent window and come into contact with the catalyst. Alternatively, light can enter the transparent window from a side, back, bottom, or corner position and move through the transparent window by a wave guide to provide photon energy and excite the light activated catalyst. Side entry of light into the transparent window of the photolytic cell occurs at about at least a 68° angle. Preferably, side entry of light into the transparent window occurs at an angle of from about 70° to about 80°.

7. Sensors Monitoring Reaction Chemistry

The apparatus can include one or more sensors that monitor the different chemical reactions occurring within the photolytic cell. The sensors can be used to measure for potential toxins and toxin levels. Various sensors and sensor systems can be used including visual observations of color changes of redox indicator dyes or gas bubble formation, closed electrical current measurements and pH measurements, and dissolved oxygen probe analysis. Gas chromatography assays can also be performed. A dissolved oxygen probe can be used to test and monitor $O_2$ generation, as dissolved oxygen, in real time. Also, the cell can incorporate one or more portals to insert a dissolved oxygen probe, $CO_2$ probe, pH monitor, etc. in different locations if necessary. The cell can also incorporate separate sampling chambers to trap gas bubbles for testing. These sampling chambers could also incorporate a device, such as a septum for a hypodermic needle for instance, to obtain a sample for further testing. One skilled in the art would recognize numerous sensors could be used for monitoring the reaction chemistries occurring within the photolytic cell.

The photolytic cell can also include one or more process regulator devices that respond to the readings provided by the sensors. The process regulator devices increase or decrease the amount of dissolved oxygen or $CO_2$ output, lower toxin levels, etc., depending on the requirements of the environment or of the photolytic cell.

Laminar flow is minimized within the apparatus. Minimization of laminar flow is accomplished by using current commercial cells, such as electrodialysis, electrodeionization, etc. Commercially available cells accommodate electrodes, membranes, and thin liquid chambers with flow distributors, and provide good seals and corrosion resistance. The cells are available in lab scale units for process development work. A particularly preferred commercial cell is the FM01-LC device from ICI Chemicals and Polymers, Electrochemical Technology, Cheshire, UK.

8. Power Source

The power source may be a nuclear reactor, electrical generator, hydroelectric energy, solar energy, battery pack, fuel cell and the like that is capable of providing energy for light production. As mentioned above, light may be from a laser, solar or other device capable of providing light at the appropriate wavelengths for the PDEC cell.

The present invention is further described with reference to several examples set forth below.

EXAMPLE 1

In this example, oxygen is produced and carbon dioxide is removed from stale air using water, $C_3$ or $C_5$ compounds and photolytic energy. Referring now to FIG. 2, a PDEC cell 16 is used for the central reaction of producing oxygen in the anode compartment 100 and producing a $C_6$ compound, such as hexose sugar, from carbon dioxide in the cathode compartment 102.

In this regard, stale air (high in $CO_2$ and low in $O_2$) 104 is first contacted with a liquid such as a recycled catholyte (e.g. aqueous phosphate with $Mg^{2+}$ catalyst) in gas/liquid contactor 106 to convert the carbon dioxide into dissolved form in the liquid, normally $CO_2$ (aq), but could also be $HCO_3$, $H_2CO_3$ and/or $CO_3^{2-}$. The gas/liquid contactor 106 can be in a counter flowing percolating bed, a micro-porous membrane, gas sparger, etc.

The dissolved carbon dioxide catalyst, glycerate, and pentose and the liquid then flow into the cathode compartment 102 of the PDEC cell 16. Pentose can also be contained in the contacting liquid catalyst. The pentose reacts with the carbon dioxide converting it to glycerate or the equivalent. The glycerate is electrochemically reduced at the surface of the cathode 108. The surface of the cathode is preferably coated with a catalyst that facilitates the hydrogenation reduction reaction such as Pb, Cd, Ni, Pd and the like. The reaction then uses the hydrogen ions that migrate across the membrane 126 from the anode compartment 110 to form a hexose sugar. The hexose sugar solution flows out of the cathode compartment 102 into a separator 112, where the liquid may be recycled and the hexose sugar placed in stores 114 or used as food for the crew, animals or microorganisms. For example the sugar-like compound, or carbohydrate-like compound, or glycerate can be recovered by crystallization, micro-filtration, electrodeionization, and the like.

The anode compartment 100 comprises the oxygen-producing portion of PDEC cell 16. Electrolyte 128 such as NaCl brine, $Na_2SO_4$, $K_2SO_4$, $H_2SO_4$, HCl, and the like flows into the anode compartment 100. The reaction of light 114 with the photoactive surface 116 comprising a photolytic catalyst and a disproportionation catalyst generates charge separation, the positive portion of which reacts with the water present in the electrolyte to form oxygen and hydrogen ions. As mentioned above, the hydrogen ions migrate into the cathode compartment 102 for further reaction. The oxygen flows out of the anode compartment 100 dissolved in the electrolyte and optionally can be allowed to coalesce into $O_2$ bubbles. The dissolved oxygen and/or $O_2$ bubbles and brine flow to an oxygen degasser or gas permeation tube 118 where the two are separated. The electrolyte is recycled to the anode compartment 100 while the oxygen flows to the enclosed volume 120 for breathing by humans, animals, microorganisms or other uses. The oxygen may also be pressurized for later use.

EXAMPLE 2

Figure 3:
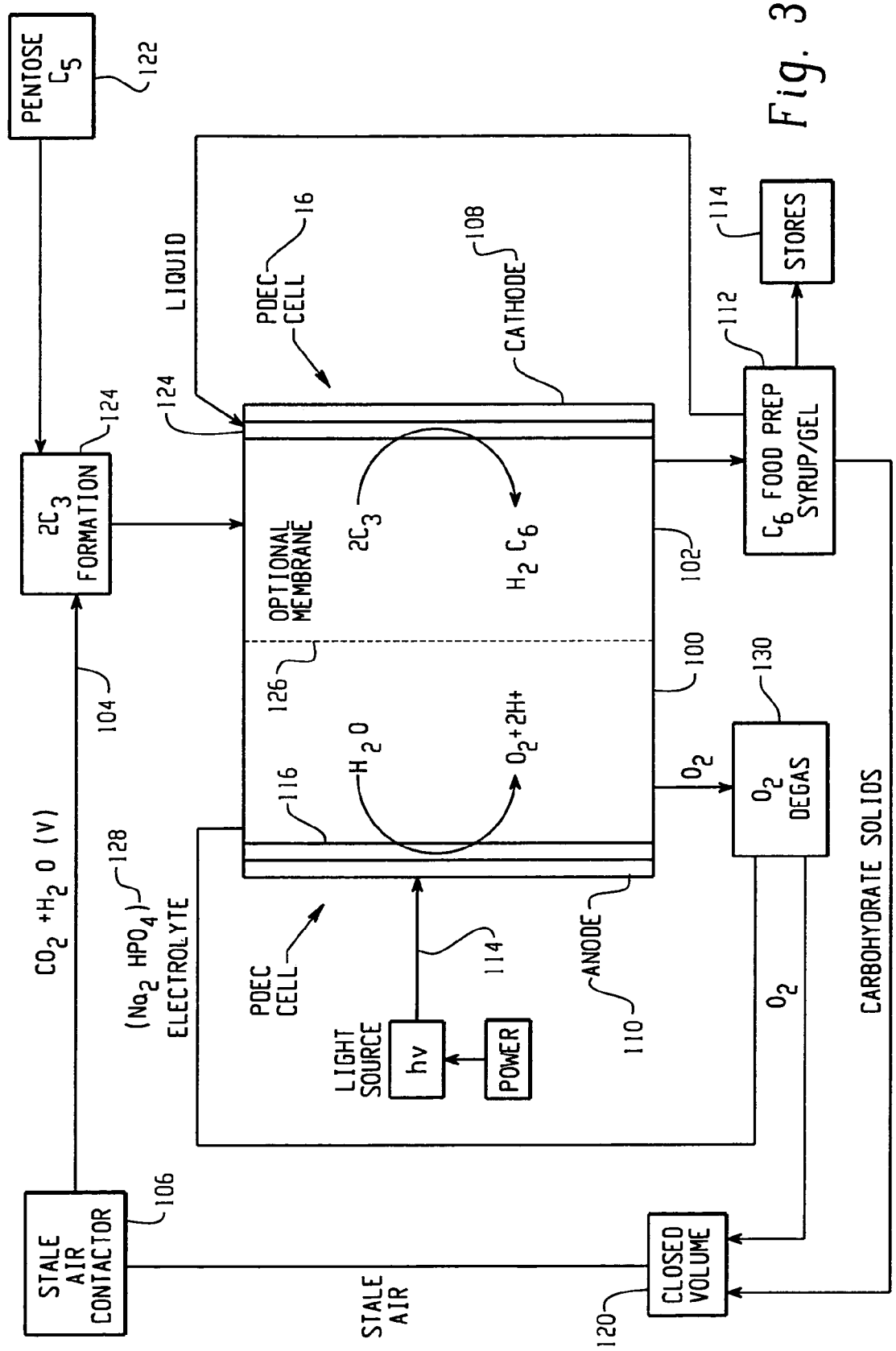
FIG. 3 is a schematic of another embodiment of the invention wherein carbon dioxide and a pentose are used to prepare a $C_3$ carbon based intermediary for carbon dioxide removal.

This example illustrates the production of oxygen and the reduction of $CO_2$ through the formation of a $C_3$ compound intermediary. Referring now to FIG. 3, a PDEC cell 16 is used for the central reaction of producing oxygen and reducing the carbon dioxide obtained from the confined space 120. Stale air 104 is first contacted with a liquid such as aqueous brine containing a α-keto pentose containing a catalyst typically of mixtures of $Mg^{2+}/PO_4^{3-}$ electrolyte gas/liquid at contactor 106 to convert the carbon dioxide into dissolved form in the liquid. This contact at contactor 106 may be in a counter flowing circulating bed, a porous membrane, or in a percolating bed, etc. The dissolved carbon dioxide, e.g. now in the carbon dioxide laden electrolyte, is also contacted with the $C_5$ pentose obtained from stores 122, also containing a catalyst, e.g. rubisco type enzymatic catalyst or a derivative compound for this enzyme. In this manner the $CO_2$ and α-keto ribulose is converted to two $C_3$ glycerate molecules at $C_3$ formulator 124. The rubisco type reaction is discussed and disclosed in reference by Garrett, Reginald et al; Biochemistry; Saunders College Publ.; pp. 720-721, (1995).

The dissolved $C_3$ compounds may then be ultra filtered to recover the enzyme and the filtrate flows to the cathode compartment 102 of the PDEC cell 16. The enzyme fraction is recycled. The enzyme may also be immobilized on a solid support or as easy-to-filter gel particles for ease of recovery/separation by means well known in the art of immobilized enzyme.

The surface of the cathode is preferably coated with a catalyst 124 that facilitates the $C_3$ to $C_6$ coupling reaction such as Ni, Pd, Pb, Cd, and the like to form sugar like compounds. The cathode compartment 102 typically uses an electro-hydrodimerization $PO_4^{3-}$ buffer at a pH of about 7 to 9 to form a hexose ($C_6$) sugar. The cathodic reaction also uses the hydrogen ions that migrate across the membrane 126 from anode compartment 100. The hexose sugar and electrolyte flow out of the cathode compartment into a separator 112, where the liquid may be recycled and the hexose sugar placed in stores 114 or used as food for the crew, animals or microorganisms.

As in Example 1 above, the anode compartment 100 comprises the oxygen-producing portion of PDEC cell. Aqueous electrolyte 128 such as $HSO_4$, $Na_2SO_4$, NaCl brine, seawater, fermentation broth, etc. flows into the anode compartment 100. In an additional benefit of the technology, the photolytic cell allows improved oxygenation of aerobic and facultative aerobic fermentations since the fiber optics arrangements can be used to disperse the oxygen uniformly and prolifically.

The reaction of light 114 with the photoactive surface 116 in the anode compartment 100 generates charge separation, the positive portion of which reacts with the water present in the electrolyte to form oxygen and hydrogen ions. As mentioned above, the hydrogen ions migrate from the anode compartment 100, across the membrane 126, into the cathode compartment 102 for further reactive use. The oxygen flows out of the anode compartment 100 dissolved in the electrolyte and optionally can be allowed to coalesce into $O_2$ bubbles. The dissolved oxygen and/or $O_2$ bubbles and brine flow to an oxygen degasser 118 or gas permeation tube where the two are separated. The electrolyte 128 is recycled to the anode compartment 100 while the oxygen flows to the enclosed volume 120 for breathing by humans, animals, microorganisms or other uses. The oxygen may also be pressurized for later use.

Figure 4:
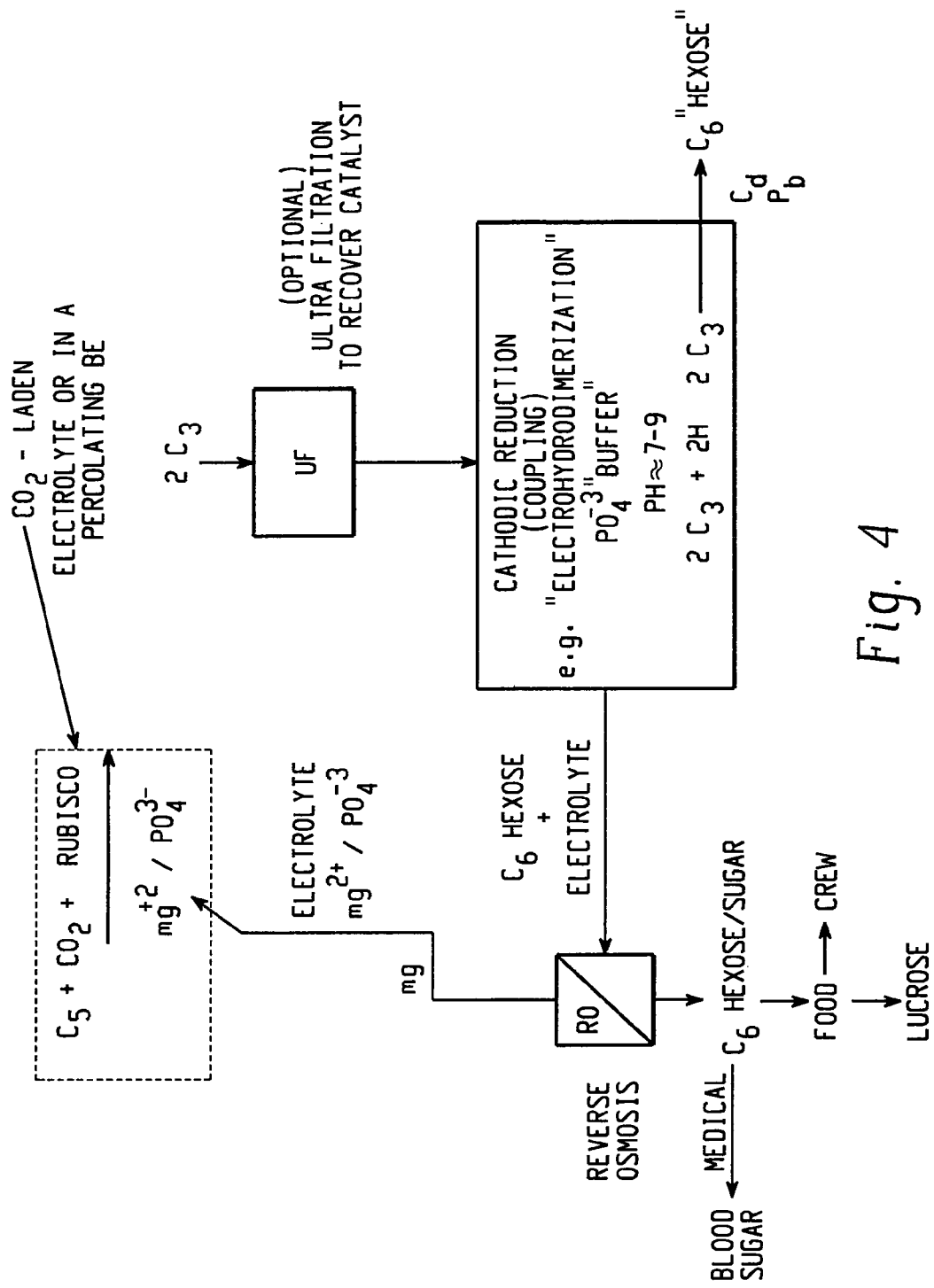
FIG. 4 is a schematic of another embodiment of the invention showing details of a rubisco-catalyzed reaction used to prepare a $C_3$ carbon intermediary for carbon dioxide removal.
Figure 5:
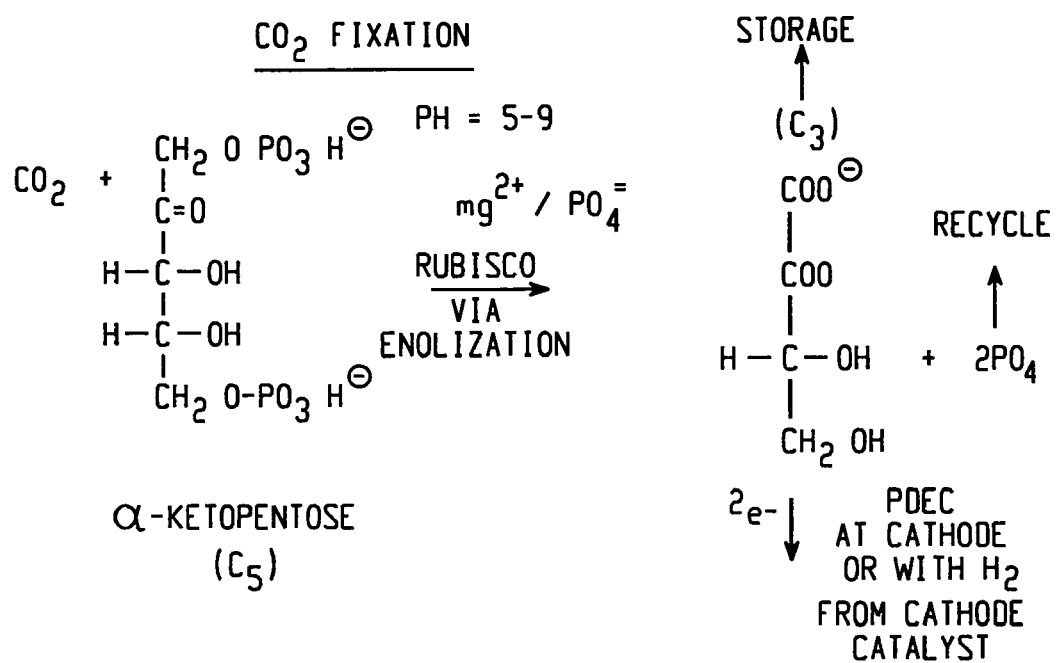
FIG. 5 is a schematic of a more detailed embodiment of the invention showing the rubisco catalyzed reaction and the chemical steps in greater detail.
Figure 5:
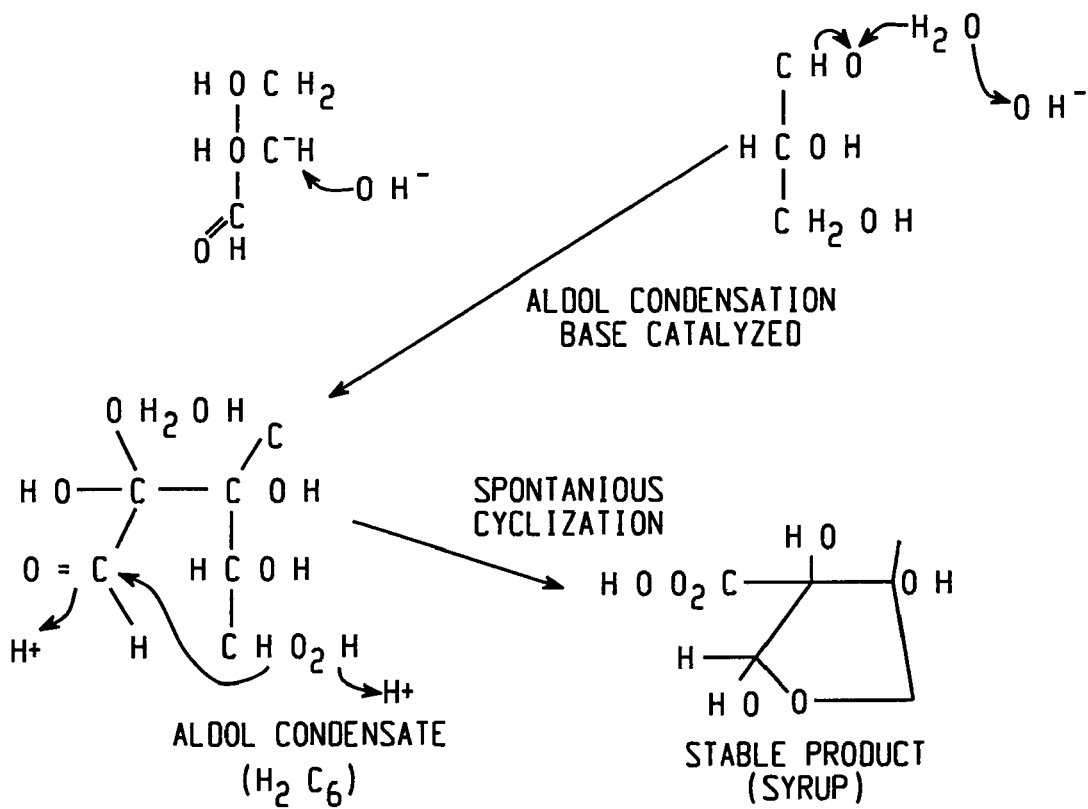
Figure 6:
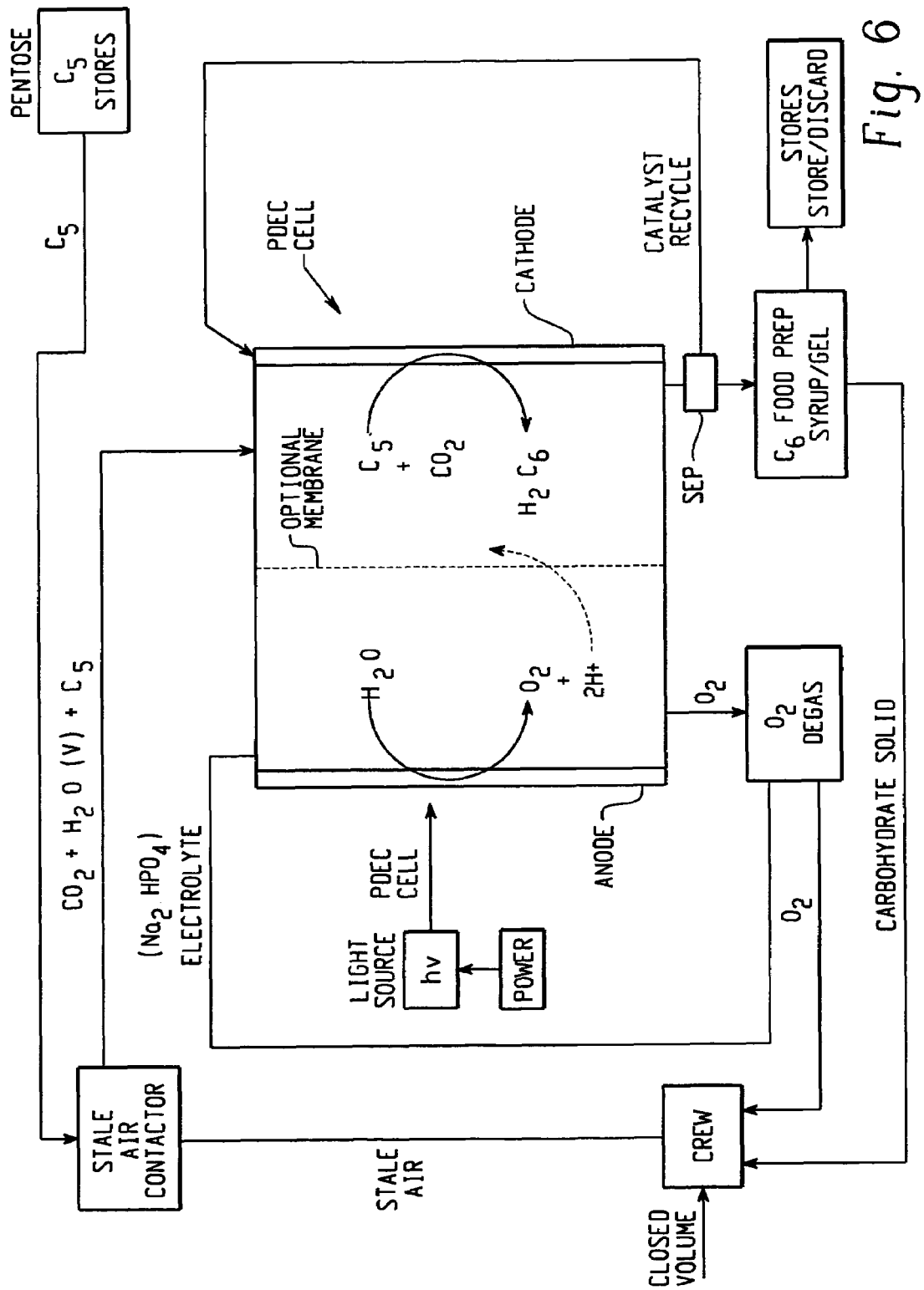
FIG. 6 is a schematic of another embodiment of the invention wherein the carbon dioxide is reacted with the pentose directly in the PDEC cell.

Other embodiments of the invention are illustrated in FIGS. 4 through 6. FIG. 4 is a schematic of an embodiment of the invention showing details of a rubisco-catalyzed reaction used to prepare a $C_3$ carbon intermediary for carbon dioxide removal. FIG. 5 is a schematic of a more detailed embodiment of the invention showing the rubisco catalyzed reaction and the chemical steps in greater detail. Moreover, FIG. 6 is a schematic of another embodiment of the invention wherein the carbon dioxide is reacted with the pentose directly in the PDEC cell.

Additionally, it is important to note that when the optional membrane 126 is not used, appropriate considertion must be given to the reactions that may occur at the electrodes taking into consideration that mixing of components may occur. In some embodiments a separator that is not a cationionic membrane may used that provides attenuated movement of materials.

Figure 7:
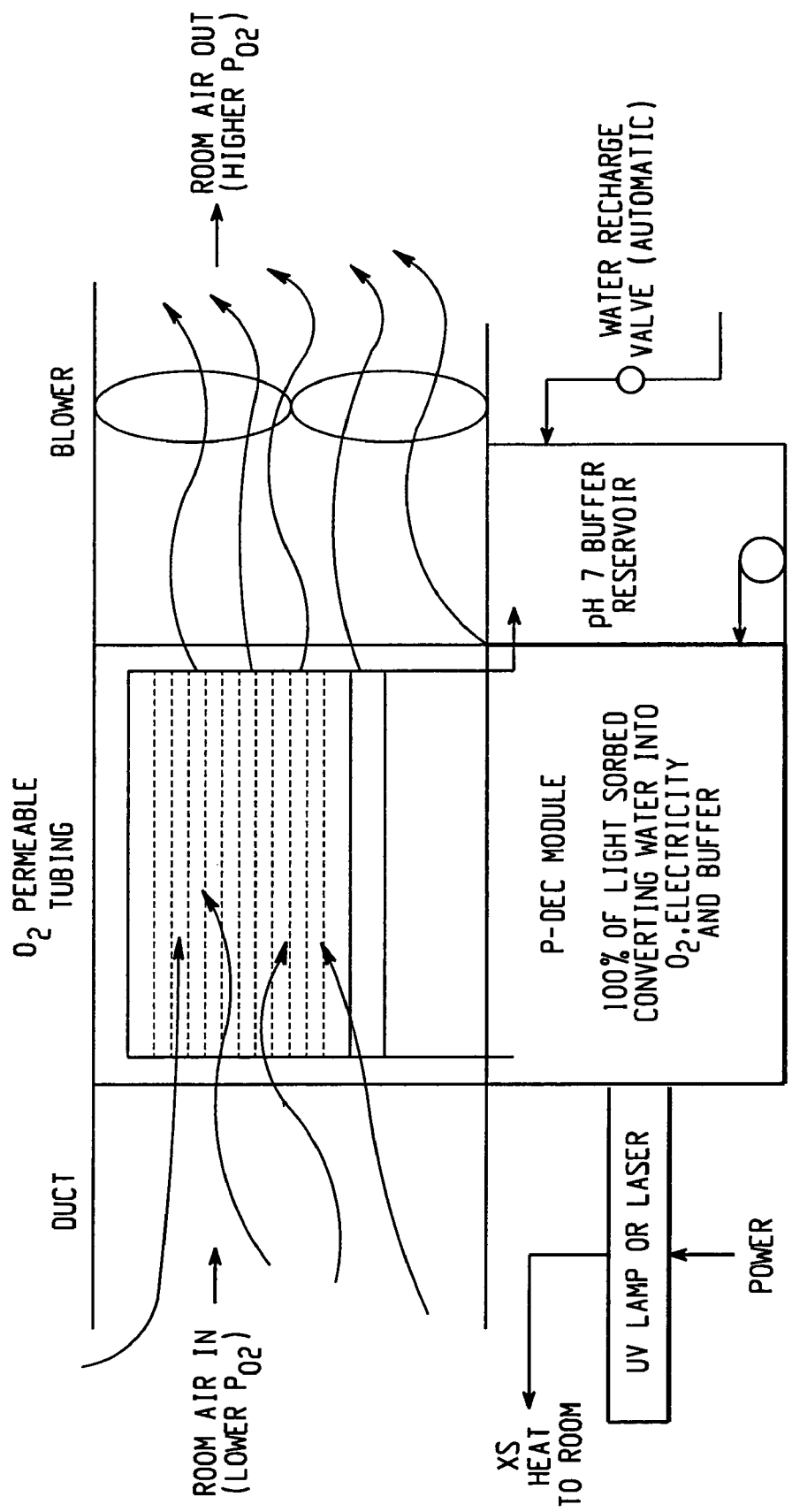
FIG. 7 is a graphic illustration demonstrating the use of a PDEC apparatus for providing oxygen in a confined environment.
Figure 8:
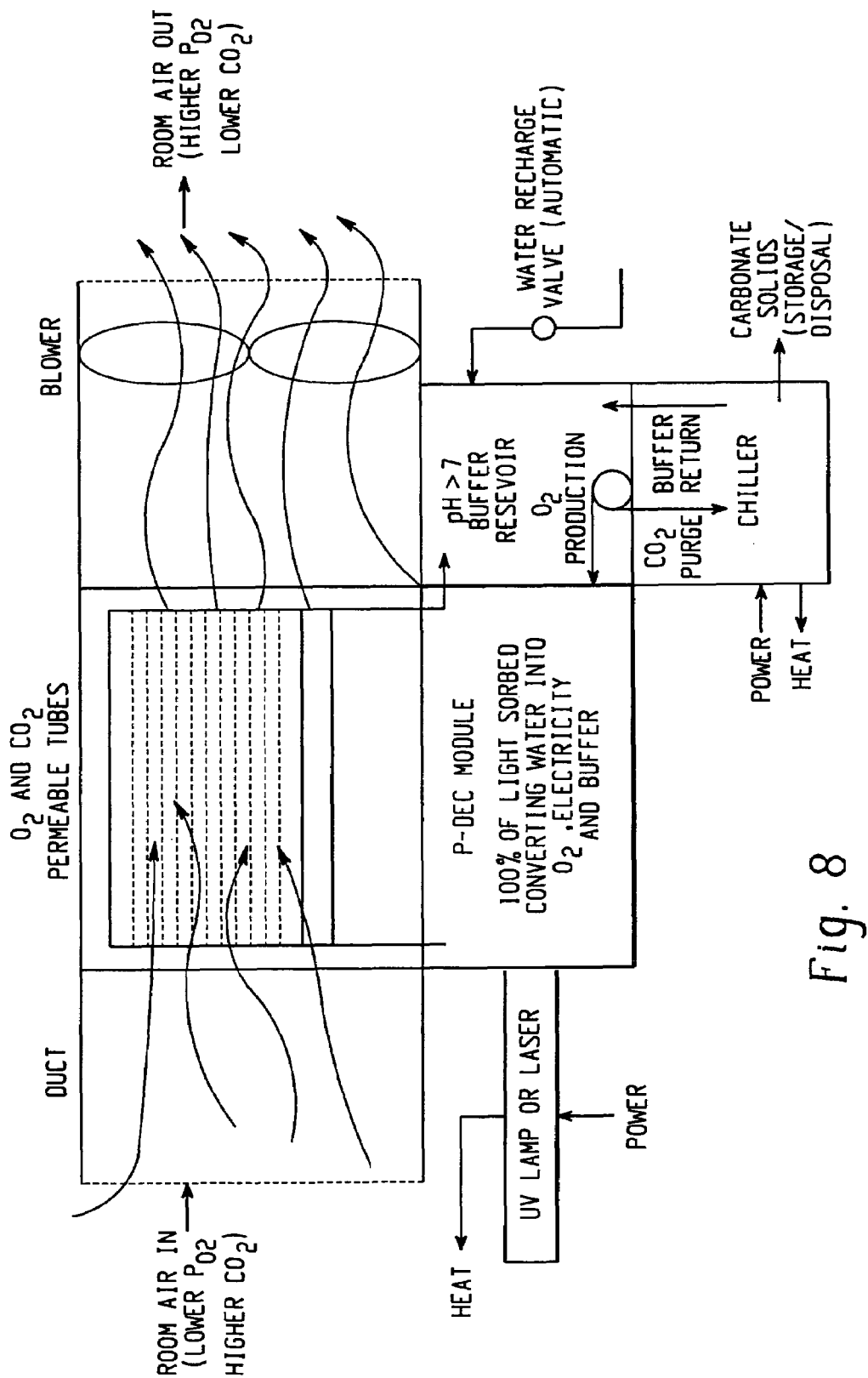
FIG. 8 is a graphic illustration showing the use of the PDEC apparatus for producing oxygen and removing carbon dioxide in a confined environment to produce a carbonate solid.
Figure 9:
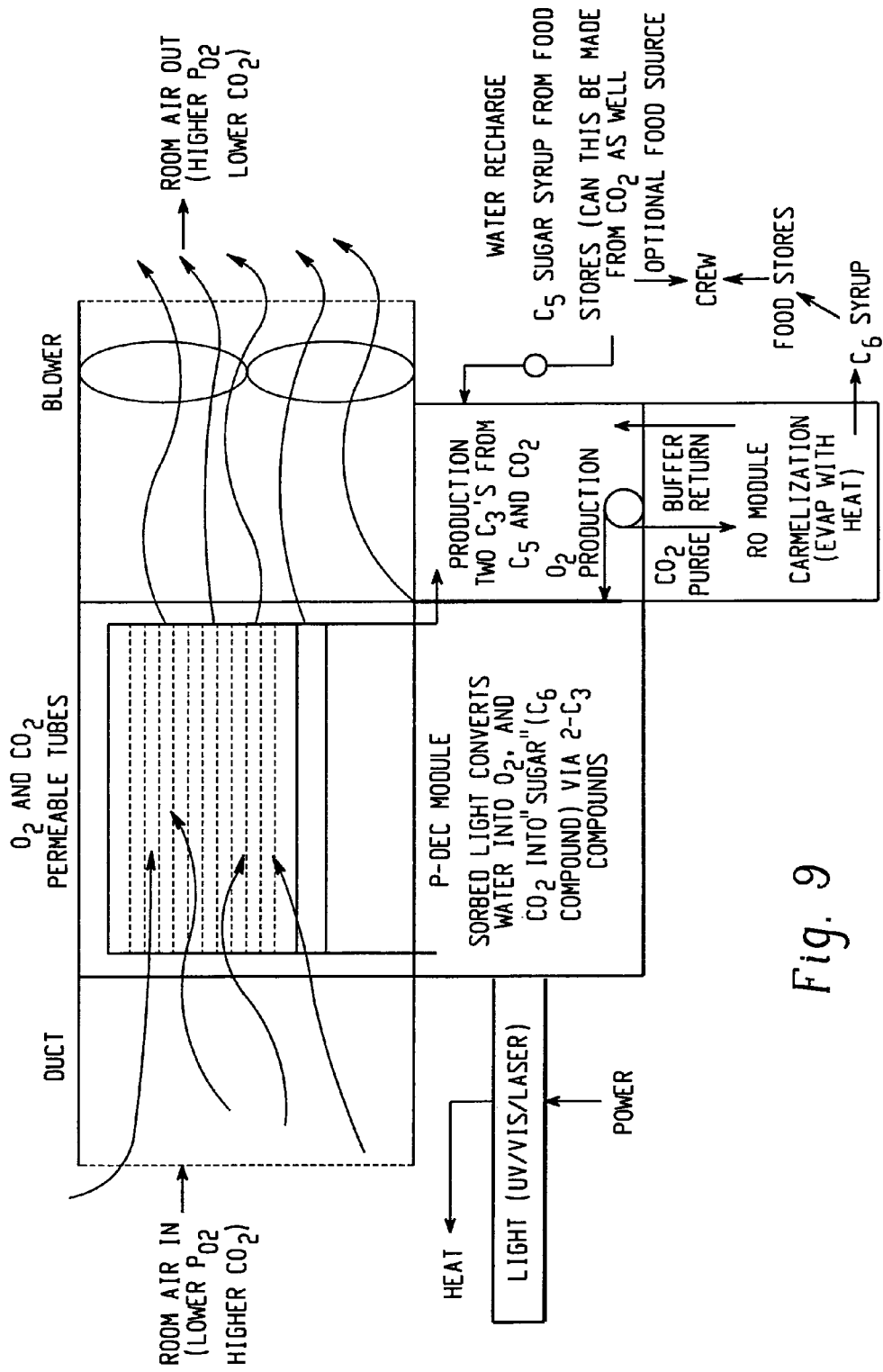
FIG. 9 is a graphic illustration demonstrating oxygen production and carbon dioxide removal by the production of $C_6$ compositions from two $C_3$ intermediaries or a $C_5$ compound and carbon dioxide.

Furthermore, FIGS. 7-9 show various embodiments of the invention incorporated into different environmental settings.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the scope of the invention.

Having thus described the preferred embodiment, the invention is now claimed to be:

1. A photolytic apparatus for oxygenating and removing carbon dioxide from a confined volume area comprising:
    a photolytic cell having an anode compartment and a cathode compartment;
        the anode compartment comprising a photo-active surface having the ability to convert water to oxygen; and
        the cathode compartment having an inlet connected to both as carbon dioxide source and a carbon source, the cathode compartment having the ability to react the carbon dioxide with the carbon source to form a solid or liquid medium; and
    a light source for providing light photons to said photolytic cell and activating the photo-reactive surface.

2. The apparatus of claim 1, wherein said photo-reactive surface comprises a light-activated catalyst.

3. The apparatus of claim 2, wherein said light activated catalyst is a metal oxide catalyst comprising anatase ($TiO_2$), $WO_3$ or ZnO, combinations thereof, with or without performance enhancing dopants.

4. The apparatus of claim 2, wherein said light-activated catalyst converts, when photolytically irradiated, water to hydrogen ions, electrons and active oxygen.

5. The apparatus of claim 4, wherein said active oxygen formed during photolysis is hydrogen peroxide or other forms of oxygen gas precursors.

6. The apparatus of claim 4, wherein said electrons generated during photolysis are then electrically conducted away to avoid reversal of the reaction.

7. The apparatus of claim 4, wherein said active oxygen formed during photolysis is converted by a disproportionation catalyst into dissolved oxygen.

8. The apparatus of claim 7, wherein said disproportionation catalyst is $MnO_2$.

9. The apparatus of claim 1, wherein said light source is an ultraviolet light at 350-500 nm.

10. The apparatus of claim 1, wherein the carbon dioxide is converted to a carbonate solid.

11. The apparatus of claim 1, wherein the carbon dioxide is reacted with $C_5$ pentose to produce $C_6$ hexose.

12. The apparatus of claim 1, wherein the carbon dioxide is converted to a $C_3$ compound and then catalyzed to form $C_6$ hexose.

13. The apparatus of claim 1, wherein the photo-reactive surface comprises a light transparent substrate and a photolytic coating.

14. The apparatus of claim 13, wherein said photolytic coating comprises a layer of a light activated catalyst which converts, when photolytically irradiated, water to hydrogen ions, electrons and active oxygen.

15. The apparatus of claim 14, wherein said photolytic coating further comprises a disproportionation catalyst which converts active oxygen to dissolved oxygen.

16. The apparatus of claim 1, wherein the anode compartment and the cathode compartment are separated by a membrane.

17. The apparatus of claim 16, wherein said membrane allows for the flow of hydrogen ions from the anode compartment to the cathode compartment.

18. The apparatus of claim 1, wherein the photolytic cell comprises a mesoporous material.

19. A photolytic apparatus for oxygenating and removing carbon dioxide in order to maintain a proper physiological environment comprising:

a photolytic cell having an anode compartment and a cathode compartment;

said anode compartment having an inlet for receiving an aqueous solution, an anode conductor, a photo-reactive surface, and an outlet for transporting a dissolved oxygenated solution out of said anode compartment, wherein said photo-reactive surface has the ability, upon photo-activation, to convert water in an aqueous solution to dissolved oxygen, hydrogen ions and electrons upon light activation;

said cathode compartment having an inlet, a cathode conductor, and an outlet, the inlet being connected to both a carbon dioxide source and a $C_5$ pentose source, the cathode conductor being able to convert hydrogen ions, carbon dioxide, and $C_5$ pentose to $C_6$ pentose, and the outlet being able to remove the $C_6$ pentose from the cell and any remaining reactants; and a light source for providing light photons to said photo-reactive surface to initiate a series of chemical reactions that results in dissolved oxygen generation in the anode compartment and $C_6$ hexose formation in the cathode compartment.

20. The apparatus of claim 19, wherein said light photo-reactive surface comprises a layer of a light activated photolytic catalyst.

21. The apparatus of claim 20, wherein said light activated photolytic catalyst is a metal oxide comprises $TiO_2$ (anatase), $WO_3$ or ZnO, or combination thereof.

22. The apparatus of claim 20, wherein said light-activated photolytic catalyst converts water into active oxygen.

23. The apparatus of claim 19, wherein said light source is an ultraviolet light at 350-500 nm.

24. The apparatus of claim 19, wherein said photo-reactive surface further comprises a disproportionation catalyst.

25. The apparatus of claim 24, wherein said disproportionation catalyst includes at least one of $Fe^{II}$, $Fe^{III}$, $Cu^{I}$, $Cu^{II}$, $Co^{II}$, $Co^{III}$, $Mn^{II}$, $M^{III}$, $Mn^{IV}$, and $MnO_2$.

26. The apparatus of claim 25, wherein said disproportionation catalyst converts active oxygen to dissolved oxygen.

27. The apparatus of claim 25, wherein said cell is constructed from mesoporous materials.

28. The apparatus of claim 25, wherein said cell is constructed of self-assembled monolayers on mesoporous supports.

29. The apparatus of claim 25, wherein said catalyst is $MnO_2$.

30. The apparatus of claim 19, wherein said photolytic cell comprises a transparent substrate and a photolytic coating comprising a first disposed layer of $TiO_2$ (anatase) and a second disposed layer of $MnO_2$.

31. The apparatus of claim 19, wherein said cell is constructed from mesoporous materials.

32. The apparatus of claim 19, wherein the anode compartment and the cathode compartment are separated by a cationic membrane.

* * * * *